United States Patent
Kik et al.

(10) Patent No.: US 7,471,388 B1
(45) Date of Patent: Dec. 30, 2008

(54) FREQUENCY TUNABLE RESONANT APPARATUS

(75) Inventors: Pieter Kik, Orlando, FL (US); Aristide Dogariu, Winter Springs, FL (US)

(73) Assignee: University of Central Florida Research Foundation, Inc., Orlando, FL (US)

( * ) Notice: Subject to any disclaimer, the term of this patent is extended or adjusted under 35 U.S.C. 154(b) by 142 days.

(21) Appl. No.: 11/472,195

(22) Filed: Jun. 21, 2006

Related U.S. Application Data

(60) Provisional application No. 60/692,898, filed on Jun. 22, 2005.

(51) Int. Cl.
*G01J 3/44* (2006.01)
*G01N 21/65* (2006.01)

(52) U.S. Cl. .................................................. 356/301

(58) Field of Classification Search .................. 356/301
See application file for complete search history.

(56) References Cited

U.S. PATENT DOCUMENTS

| | | | | |
|---|---|---|---|---|
| 4,343,993 A * | 8/1982 | Binnig et al. | ................ | 250/306 |
| 5,025,147 A * | 6/1991 | Durig et al. | ................. | 250/216 |
| 5,629,951 A * | 5/1997 | Chang-Hasnain et al. | ..... | 372/20 |
| 5,739,945 A * | 4/1998 | Tayebati | ..................... | 359/291 |
| 5,771,253 A * | 6/1998 | Chang-Hasnain et al. | ..... | 372/20 |
| 6,180,415 B1 * | 1/2001 | Schultz et al. | .............. | 436/518 |
| 6,331,276 B1 * | 12/2001 | Takei et al. | .............. | 422/82.09 |
| 6,867,900 B2 * | 3/2005 | Weisbuch et al. | ........... | 359/321 |
| 7,177,021 B2 * | 2/2007 | Wang et al. | .................. | 356/301 |
| 7,307,719 B2 * | 12/2007 | Wang et al. | .................. | 356/301 |

OTHER PUBLICATIONS

Michaels, et al., *Surface Enhanced Raman Spectroscopy of Individual Rhodamine 6G Molecules on Large Ag Nanocrystals*, J. Am. Chem. Soc. vol. 121 (43), (1999), pp. 9932-9939.
Muller, et al., Electrically Controlled Light Scattering with Single Metal Nanoparticles, Appl. Phys. Lett., vol. 81, No. 1, Jul. 1, (2002), 3 pages.
H. Ditlbacher, et al., "*Two-dimensional optics with surface plasmon polaritions,*" Applied Physics Letters, vol. 81, No. 10, Sep. 2, 2002, pp. 1762-1764.
Christy L. Haynes, et al., "*Plasmon-Sampled Surface-Enhanced Raman Excitation Spectroscopy,*" J. Phys. Chem. B (2003) vol. 107, pp. 7426-7433.

* cited by examiner

*Primary Examiner*—F. L Evans
(74) *Attorney, Agent, or Firm*—Brian S. Steinberger; Phyllis K. Wood; Law Offices of Brian S. Steinberger, P.A.

(57) ABSTRACT

Tuning of the resonant state of a structure that scatters optical fields is achieved by varying the effective optical properties of the environment of a small conductive structure. The frequency tunable resonant scatterer includes a medium, a conductive structure within that medium and a second structure in the vicinity of said conductive structure, wherein the plasmon resonance of said conductive structure is tuned by way of the proximity of said second structure to said conductive structure. The second structure is gradually moved away from and closer to the nanoparticle to change the effective dielectric constant for tuning a resonance frequency of the conductive structure to plural excitation wavelengths.

16 Claims, 3 Drawing Sheets

FREQUENCY TUNABLE RESONANT APPARATUS

This application claims the benefit of priority to U.S. Provisional Patent Application No. 60/692,898 filed on Jun. 22, 2005.

FIELD OF THE INVENTION

This invention relates to the scattering of optical fields using conductive structures, in particular to methods, systems and devices for enhancing optical emissions by tuning the resonant states of the conductive structures for applications including miniature biochemical detector arrays, high resolution displays, optical displacement sensors, microphone arrays, and tunable waveguide filters.

BACKGROUND AND PRIOR ART

In many applications, the sensing, manipulation, and display of optical information are based on scattering of optical fields with specific frequencies on various scattering structures. These actions are significantly more efficient when the scatterer is brought into a resonant regime.

Metals, or more generally conductors, exhibit special optical properties due to the existence of coherent charge density oscillations. On surfaces these take the form of propagating waves known as surface plasmons. Similarly, conductive structures can exhibit collective electron oscillations at frequencies determined by the shape, size, composition, crystallinity, and environment of the structure. For example, in metal nanoparticles these collective oscillations lead to pronounced resonances at optical frequencies. These resonances become apparent in extinction measurements due to resonantly enhanced scattering and absorption. A prior art example is shown in the graph of FIG. 1, which shows experimental data on the optical transmission of 41 nm diameter silver nanoparticles in an aqueous solution. The extinction peak at approximately 410 nm is caused by the plasmon resonance in the silver nanoparticles.

Associated with these resonances are localized electromagnetic fields with significantly enhanced field strength relative to that of the excitation source. An example is shown in FIG. 2, which shows a calculated snapshot 200 of the energy density around a metal nanoparticle under plane-wave illumination at the surface plasmon resonance frequency. Field enhancements can be as large as several orders of magnitude. The ability to actively control these resonances could play an important role in applications that benefit from enhanced electric fields, enhanced localization of light, enhanced optical absorption, or enhanced optical scattering.

One application in which this field enhancement plays an important role is Surface Enhance Raman Spectroscopy (SERS). Raman scattering involves the excitation or annihilation of phonons upon laser illumination of certain materials, resulting in the appearance of photons with a slightly modified energy. By measuring the energy distribution of the scattered laser light, information can be obtained about the structure of the object, allowing for identification of the scattering element.

Although Raman scattering has been shown to yield identifiable molecular vibration spectra, the signal strength is typically low, making the detection of low concentrations of molecules difficult. It has been found however that the strength of the Raman signal from a given molecule can be enhanced by factors in excess of $10^{10}$ near the surface of a resonantly excited metal nanoparticle, as discussed by Michaels et al. in Surface Enhanced Raman Spectroscopy of Individual Rhodamine 6G Molecules on Large Ag Nanocrystals, J. Am. Chem. Soc. 121, 9932 (1999). The magnitude of the signal enhancement makes SERS a viable technique for performing high sensitivity chemical detection.

Surface Enhance Raman Scattering can occur at frequencies where metal nanostructures exhibit plasmon resonances. In experiments, an excitation wavelength as short as possible is chosen because the strength of the Raman signal depends to the fourth power on the frequency of the excitation source. However, at short excitation wavelengths, many molecules show bright fluorescence that can make the weak Raman signal difficult to detect. Consequently, for each molecule, it is necessary to determine the shortest possible excitation wavelength and design the corresponding metal structure to obtain SERS at that wavelength.

A second example where tunability is desired is the case of Surface Enhanced Resonant Raman Scattering (SERRS). It has been observed that Raman signals can be further enhanced in specific situations where the excitation wavelength overlaps with an absorption band of the species under investigation. In these cases, the resonance of the metal nanostructure must be tuned to match the energy of the desired molecular transition, requiring a broad range of resonance frequencies to be covered.

SERRS requires a tailored conductive nanostructure, e.g. a metal nanoparticle, for each species that needs to be detected. This approach is feasible when a single species needs to be detected, but rapidly becomes impractical when multiple species are involved. In the latter case, it would be beneficial to be able to tune the resonance frequency of the metal nanostructure to coincide with several different excitation wavelengths, enabling the detection of several species within a small detection volume. This would allow the design of compact biochemical sensors for multi-species detection.

Thus, there exists a need to be able to actively tune the resonant frequency of a metal nanoparticle to a broad range of frequencies that has not been achieved in the prior art.

SUMMARY OF THE INVENTION

The first objective of the present invention is to provide apparatus, methods, systems and devices for frequency tunable resonant apparatus.

A second objective of the present invention is to provide apparatus, methods, systems and devices to tune the resonance frequency of a conductive structure.

A third objective of the present invention is to provide apparatus, methods, systems and devices for building frequency tunable resonant scatterers based on varying the effective optical properties of the environment of a small conductive particle.

A fourth objective of the present invention is to provide apparatus, methods, systems and devices to provide frequency tunable resonant scatterer with significant benefits including sensitivity, selectivity, and integrability with microscopic structures.

A fifth objective of the present invention is to provide apparatus, methods, systems and devices to tune the resonance frequency of a conductive structure such as metal nanoparticles, to a broad range of different excitation wavelengths.

A sixth objective of the present invention is to provide apparatus, methods, system and devices to tune the resonant frequency of a metal nanostructure by varying the environment of the nanostructure.

A seventh objective of the present invention is to provide apparatus, methods, system and devices for continuous tuning over a larger range—greater than 100 nm—than was previously possible.

An eighth objective of the present invention is to provide apparatus, methods, system and devices for using a conductive nanostructure with a particular engineered shape to improve performance according to a particular application.

A first embodiment of the invention provides a frequency tunable resonant scatterer comprising a medium with a conductive structure embedded therein and a second structure in a vicinity of the conductive structure so that the plasmon resonance of the conductive structure is tuned according to the proximity of the second structure to the conductive structure.

In another embodiment of the present invention, the frequency tunable resonant apparatus includes a medium with conductive nanostructures embedded in the medium and a cantilever in the vicinity of said conductive nanostructure, wherein the plasmon resonance of the conductive nanostructure is tuned by way of the proximity of the cantilever to the conductive nanostructure. In an embodiment, the conductive nanostructure or the nanoparticle has a diameter smaller than an excitation wavelength of the conductive structure or the nanostructure, wherein the cantilever is moved within a proximity of said nanostructure to tune the resonance frequency to several different excitation wavelengths, enabling the detection of several species with the nanostructure. In an embodiment, the medium is a top and bottom silicon oxide substrate and the cantilever is a layer of silicon material, wherein the layer is sufficiently thin to render the silicon layer transparent to wavelengths greater than approximately 400 nanometers.

A second embodiment provides a tunable optical sensing method, comprising the steps of providing a medium, the medium having a plurality of metal nanoparticles, providing at least one cantilever in the vicinity of said plural nanoparticles, exciting the medium with a light source, varying an effective optical property of an environment in which said plural nanoparticles are located for continuous tunability; and detecting light scattered from said plural nanoparticles. The apparatus, methods, systems and devices of the present invention have applications including miniature biochemical detector arrays, high resolution displays, optical displacement sensors, microphone arrays, and tunable waveguide filter.

Further objects and advantages of this invention will be apparent from the following detailed description of the presently preferred embodiments which are illustrated schematically in the accompanying drawings.

DESCRIPTION OF THE PREFERRED EMBODIMENT

Before explaining the disclosed embodiment of the present invention in detail it is to be understood that the invention is not limited in its application to the details of the particular arrangement shown since the invention is capable of other embodiments. Also, the terminology used herein is for the purpose of description and not of limitation.

Figure 1:
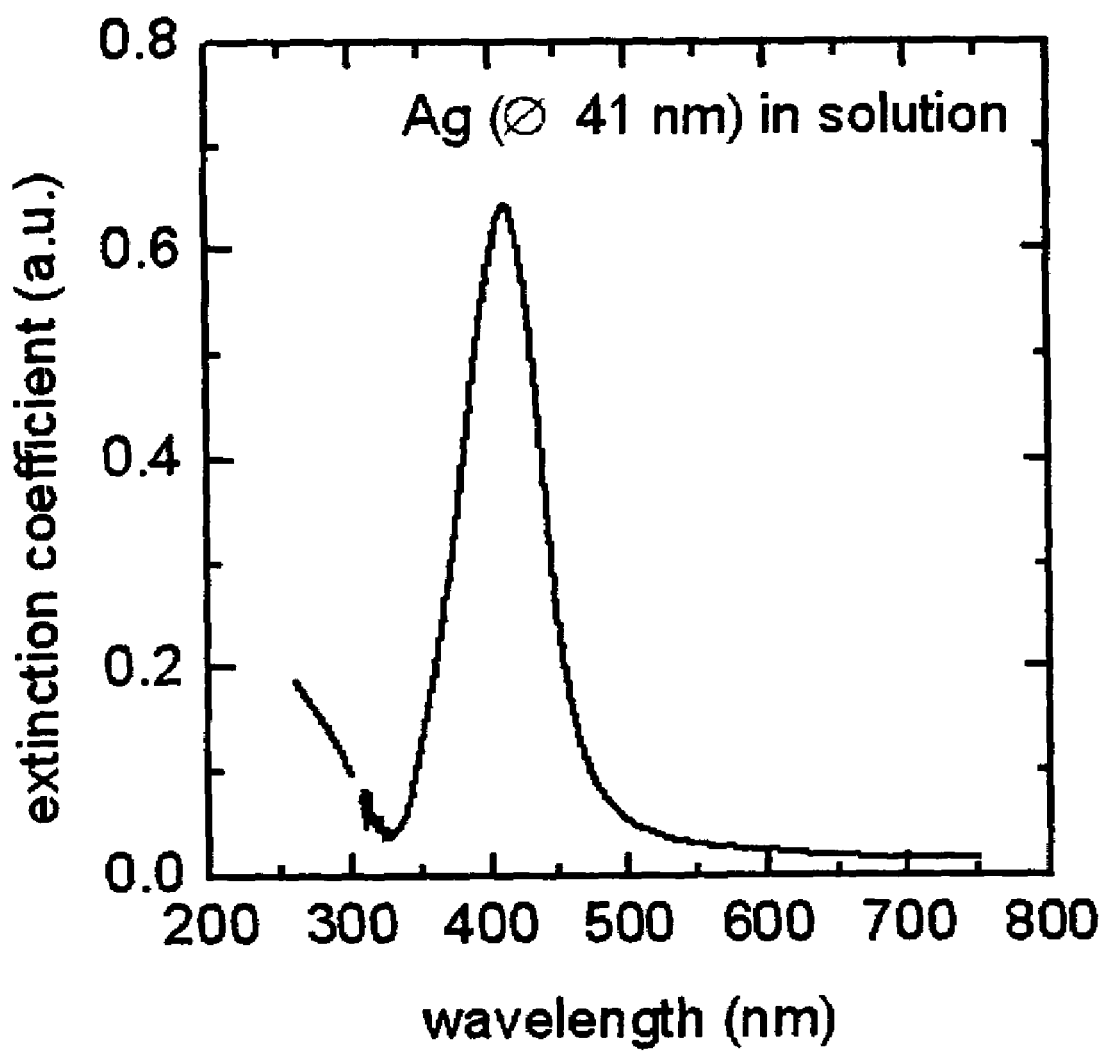
FIG. 1 shows extinction measurement on an aqueous solution of 41 nm diameter silver (Ag) nanoparticles exhibiting a plasmon resonance related extinction peak at 410 nm.
Figure 2:
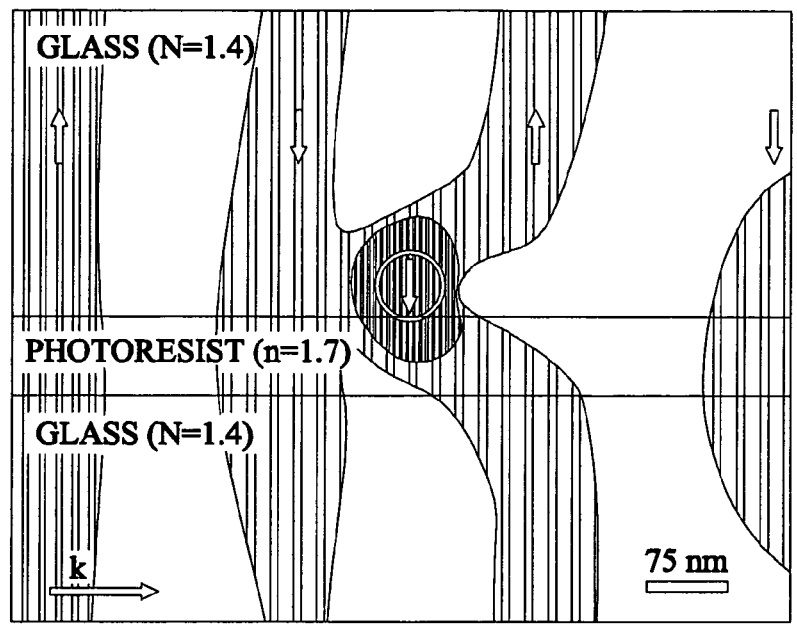
FIG. 2 shows a Finite Difference Time Domain calculation of the energy density around a metal nanoparticle under plane wave excitation.

To understand the opportunities in tuning plasmon resonances, consider the conditions under which resonant behavior of metal nanoparticles occurs. The Mie theory describes the scattering of light by particles. The Mie theory, also called the Lorenz-Mie theory, is a complete mathematical-physical theory of the scattering of electromagnetic radiation by spherical particles. From Mie theory it follows that the polarizability of a nanosphere with a diameter much smaller than the excitation wavelength is given by:

$$\alpha = 4\pi\varepsilon_0 R^3 \frac{\varepsilon - \varepsilon_m}{\varepsilon + 2\varepsilon_m} \quad (1)$$

where $\varepsilon_m$ is the dielectric function of the medium in which the particle is embedded, and $\varepsilon$ is the dielectric function of the particle. The polarizability diverges for $\varepsilon=-2\varepsilon_m$. For silver nanoparticles in water this condition occurs at a wavelength of approximately x=410 nm as shown in the graph of FIG. 1. Due to its dependence on $\varepsilon_m$ (and thus the refractive index) the resonance frequency can be tuned over a small range by tuning the dielectric constant of the medium. For example, by changing the refractive index of the medium from 1.4 to 1.5, the silver nanoparticle resonance can be shifted from 390 nm to 400 nm. This shift in resonance frequency is insufficient to accommodate a wide range of molecular absorption lines, even though the change in refractive index is much larger than what can be achieved in optical nonlinear materials or liquid crystals.

Tuning of plasmon resonances of particles embedded in a continuous medium by changing the refractive index of surrounding material was shown by Muller et al. in Electrically Controlled Light Scattering with Single Metal Nanoparticles, Appl. Phys. Lett. 81, 171 (2002). Due to the limited range of accessible refractive indices, the tuning was limited to a small wavelength range of 15 nm. To obtain tunability over hundreds of nanometers, the dielectric function of the environment needs to be modulated by several tens of percents, which is not readily achieved with common optical materials.

Figure 3A:
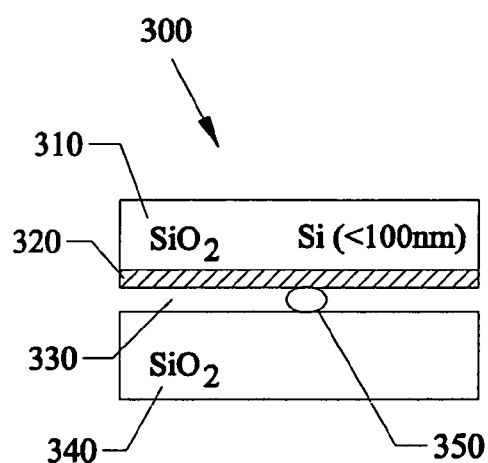
FIG. 3a shows a schematic of a MEMS (Micro-Electro-Mechanical Systems) structure allowing continuous tunability of a metal nanoparticle plasmon resonance in a first state.
Figure 3B:
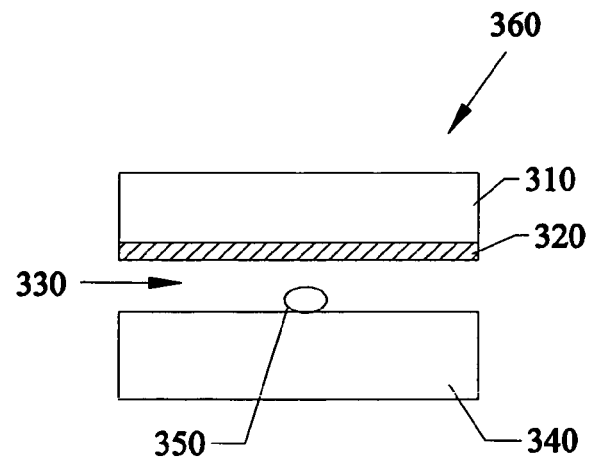
FIG. 3b shows a schematic of a MEMS (Micro-Electro-Mechanical Systems) structure allowing continuous tunability of a metal nanoparticle plasmon resonance in a second state

Broadband tuning of the plasmon resonance is obtained by changing the environment 330 of a metal nanoparticle 350 from air ($\varepsilon\sim 1$) to silicon ($\varepsilon=14$). FIGS. 3a and 3b show a MEMS structure of the frequency tunable resonant scatterer including a top substrate 310 with a thin cantilever layer 320 the inner surface of the top substrate 310. A bottom substrate 340 separated from the top substrate 310 by a distance sufficient for positioning the nanopartical 350 on the bottom substrate 340. FIG. 3a shows the structure in a first state having a high local index and a long resonant wavelength and FIG. 3b shows the structure during a second state having a low local index and a short resonant wavelength.

By moving the movable structure, a silicon (Si) cantilever 320 in this example, close to a conductive structure 350 positioned on a low index substrate 340 such as $SiO_2$, as shown in FIG. 3, a radical change of dielectric constant is achieved. In this example, the effective dielectric constant can be modulated from an $SiO_2$—air environment with an effective dielectric constant $$\varepsilon_{\it eff} \approx \frac{1}{2}(\varepsilon_{air} + \varepsilon_{SiO_2}) = 1.5$$

to an $SiO_2$—Si environment with $\in_{\it eff}\approx\frac{1}{2}(\in_{Si}+\in_{SiO2})=8.6$. The Si cantilever 320 can be made thin enough to render the Si transparent to wavelengths larger than 400 nm, while still providing the high refractive index to obtain substantial resonance wavelength tuning. Continuous tunability is achieved by gradually moving the Si cantilever away from the conductive structure, changing the effective dielectric constant from 8.6 to 1.5. This type of continuous movement of Si membranes can be achieved with MicroElectro-Mechanical Systems (MEMS) technology.

Figure 4:
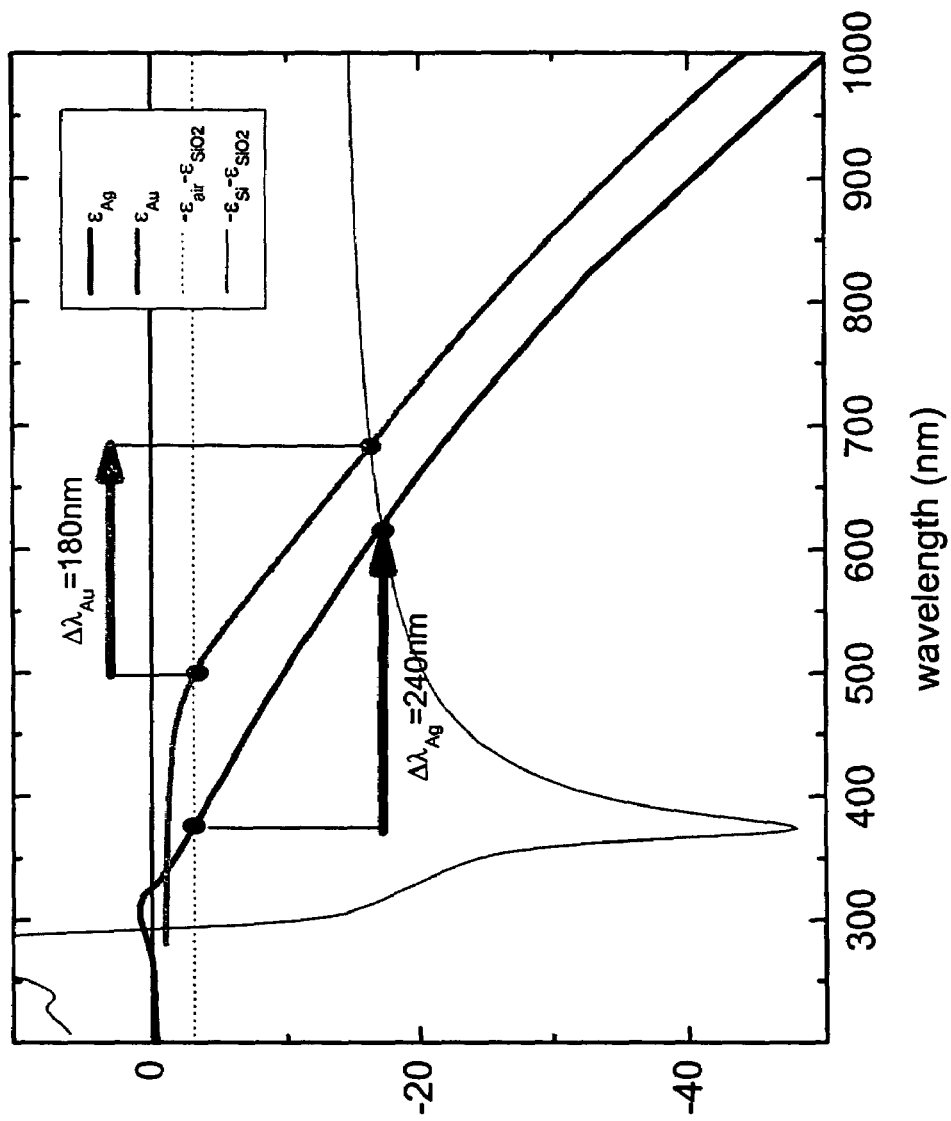
FIG. 4 is a graph showing an example of the tuning range available for gold or silver nanoparticles on silicon-oxide (SiO$_2$) using a silicon (Si) cantilever.

The achievable tuning range in different materials systems is determined by comparing the frequency dependent dielectric functions of the metal, the substrate, and the cantilever. To obtain a nanoparticle resonance, it is necessary to satisfy the requirement $\in_{metal}=-2\times\in_{\it eff}$ where $\in_{metal}$ is the dielectric function of the particle, and $\in_{\it eff}$ is the device state dependent average $\in$ near the particle. In state one shown in FIG. 3*a*, this corresponds to the condition $\in_{metal}\approx-\in_{substrate}-\in_{cantilever}$ with $\in_{substrate}$ the dielectric function of the substrate immediately beneath the particle, and $\in_{cantilever}$ the dielectric function of the high refractive index layer directly above the particle as shown in FIG. 3. In state 2, shown in FIG. 3*b*, this leads to the requirement $\in_{metal}\approx-\in_{substrate}-\in_{air}$. These conditions can be graphically depicted by plotting both sides of the equation, and locating the crossing points as shown in FIG. 4, for a gold particle and a silver particle. The resonance conditions are indicated by dots, with the long-wavelength solution corresponding to state 1 shown in FIG. 3*a*. From this graph it can be seen that shifts in excess of 200 nm can be obtained using existing materials.

The present invention has a wide range of potential applications including biochemical detectors, high resolution displays, acoustic sensors, waveguide filters, and optical traps. The broad tuning range of the conductive structure resonances allows for the detection of a wide range of molecular species by a single set of conductive structure utilizing Surface Enhanced Raman Scattering. The molecular detector could have a footprint of a few square microns, making the fabrication of detector arrays a clear possibility. High resolution displays can be developed in which conductive nanoparticles act a tunable scatterers, allowing for nanoscale pixels covering the RGB range. The frequency of scattered light provides a sensitive probe of the distance between the Si membrane and the metal particle and thus allows for the development of nanoscale passive acoustic sensors.

Scatterers on a waveguide can be turned on or off by moving a Si cantilever, thus providing a continuously tunable waveguide filter with a blocking band over a greater than 200 nm range. The resonantly excited local fields near metal nanoparticles can be used to trap polarizable objects thus becoming a tunable optical trap. Frequency control of the resonances would provide control over the molecular species that is trapped.

A second embodiment provides a tunable optical sensing method by providing a medium with a plurality of conductive structures, a cantilever in the vicinity of the plural conductive structures, such as conductive nanoparticles, exciting the medium with a light source, varying an effective optical property of an environment in which said plural conductive structures are located for continuous tunability and detecting light reflected from said plural conductive nanoparticles. The effective optical property is varied by gradually moving the cantilever away from or close to the plural conductive nanoparticles to change the effective dielectric constant for tuning a resonance frequency of the plural conductive nanoparticles to plural excitation wavelengths, wherein the frequency tunable resonant scatterer provides high sensitivity and selectivity.

While the invention has been described, disclosed, illustrated and shown in various terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

We claim:

1. A frequency tunable resonant apparatus comprising:
   a top substrate and a bottom substrate separated by a distance;
   a nanostructure having a diameter smaller than an excitation wavelength of the nanostructure; and
   a movable silicon cantilever in a vicinity of said nanostructure between said top and said bottom substrate, wherein a plasmon resonance of said nanostructure is tuned to several different excitation wavelengths according to a proximity of said movable silicon cantilever to said nanostructure enabling the detection of several species with said nanostructure.

2. The frequency tunable resonant apparatus of claim 1, further comprising:
   one of an enhanced electric field, enhanced localization of light, enhanced optical absorption and an enhanced optical scattering for using the frequency tunable resonant apparatus.

3. The frequency tunable resonant apparatus of claim 1, wherein the frequency tunable resonant apparatus comprises:
   a frequency tunable resonant scatterer.

4. The frequency tunable resonant apparatus of claim 1, wherein said top and said bottom substrate comprise:
   a top silicon oxide layer having a thin silicon layer on the interior surface of the top silicon oxide substrate; and
   a bottom silicon oxide layer.

5. The frequency tunable resonant apparatus of claim 1, wherein the movable silicon cantilever comprises:
   a layer of silicon material, wherein the layer is sufficiently thin to render the silicon layer transparent to wavelengths greater than approximately 400 nanometers.

6. The frequency tunable resonant apparatus of claim 1, wherein said a nanostructure comprises:
   a material selected from at least one of silver and gold.

7. The frequency tunable resonant apparatus of claim 1, further comprising:
   a device for moving said movable silicon cantilever within the proximity of said a nanostructure.

8. The frequency tunable resonant apparatus of claim 1, wherein said a nanostructure comprises:
   a shape selected to improve performance according to a particular application of the frequency tunable resonant apparatus.

9. A tunable optical sensing method, comprising the steps of:
   providing a medium consisting of top and bottom substrate separated by a distance and having a plurality of conductive nanostructures therebetween;
   providing at least one movable member in a vicinity of said plural conductive nanostructures between the top and bottom substrate;
   exciting the medium with a light source;
   varying an effective optical property of an environment in which said plural conductive nanostructures are located for continuous tenability by moving the at least one movable member to tune a resonance frequency to several different excitation wavelengths, enabling the detection of several species with a single conductive nanostructure; and
   detecting light reflected from said plural conductive nanostructures.

10. The method of claim 9, wherein the detecting step comprises:
   detecting Raman signals.

11. The method of claim 9, wherein varying an effective optical property comprises the step of:
   gradually moving the at least one movable member away from the plural conductive nanostructures to change the effective dielectric constant for tuning a resonance frequency of the plural conductive nanostructures to plural excitation wavelengths.

12. The method of claim 9, wherein varying an effective optical property comprises the step of:
   gradually moving the at least one movable member close to the plural conductive nanostructures to achieve a radical change of dielectric constant for tuning a resonance frequency of the plural conductive nanostructures to plural excitation wavelengths, wherein the frequency tunable resonant scatterer provides high sensitivity and selectivity.

13. The method if claim 9, further comprising the step of: integrating an optical sensor with a microscopic structure.

14. The method of claim 9, further comprising the step of: using a Micro Electro Mechanical System technology to continuously move the at least one movable member.

15. The method of claim 9, further comprising the step of: using the tunable optical sensing device as a compact biochemical sensor for multi-species detection.

16. The method of claim 9, further comprising the step of: selecting a shape of said conductive nanostructure to improve performance according to a particular application for using the optical sensing method

* * * * *